United States Patent [19]
Bak et al.

[11] Patent Number: 5,453,563
[45] Date of Patent: Sep. 26, 1995

[54] GUZMANIA PLANT NAMED 'ULTRA'

[75] Inventors: Geradus J. Bak, Assendelft; Nicolaas D. Steur, Oude Niedorp; Elly Bak, Rijsenhout, all of Netherlands

[73] Assignee: Corn. Bak B.B., Assendelft, Netherlands

[21] Appl. No.: 11,693

[22] Filed: Feb. 1, 1993

Related U.S. Application Data

[63] Continuation of Ser. No. 765,005, Sep. 24, 1991, Pat. No. P.P. 8,221.

[51] Int. Cl.⁶ .................................. A01H 5/00; A01H 5/10
[52] U.S. Cl. .......................... 800/200; 800/250; PLT/88.8
[58] Field of Search ..................................... PLT/88.1, 88.6, PLT/88.8; 800/200, 205, 250, DIG. 54

[56] References Cited

U.S. PATENT DOCUMENTS

PP. 8,221  5/1993  Bak et al. ............................... PLT/88.8

*Primary Examiner*—David T. Fox
*Assistant Examiner*—Erich E. Veitenheimer
*Attorney, Agent, or Firm*—Foley & Lardner

[57] ABSTRACT

A new cultivar of Guzmania named 'U', characterized by its purple, star shaped inflorescence, superior floral bract production, strong, compact growth habit, and its relatively small size.

2 Claims, 3 Drawing Sheets

GUZMANIA PLANT NAMED 'ULTRA+2

CROSS-REFERENCE TO RELATED APPLICATION

This application is a continuation of application Ser. No. 07/765,005, filed on Sep. 24, 1991, now U.S. Pat. No. 8,221.

BACKGROUND OF THE INVENTION

Guzmania comprise a genus within the family Bromeliaceae, with the genus constituting over 100 species of evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania varies considerably but is generally in the orange, red and red-purple ranges. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

SUMMARY OF THE INVENTION

The present invention relates to a new and distinct cultivar of *Guzmania ligulata,* hereinafter referred to by the cultivar name 'Ultra'. The new cultivar is a hybrid resulting from a cross of unnamed parent plants identified below.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The accompanying color photographic drawings show typical characteristics of 'Ultra'.

DETAILED DESCRIPTION

Figure 1:
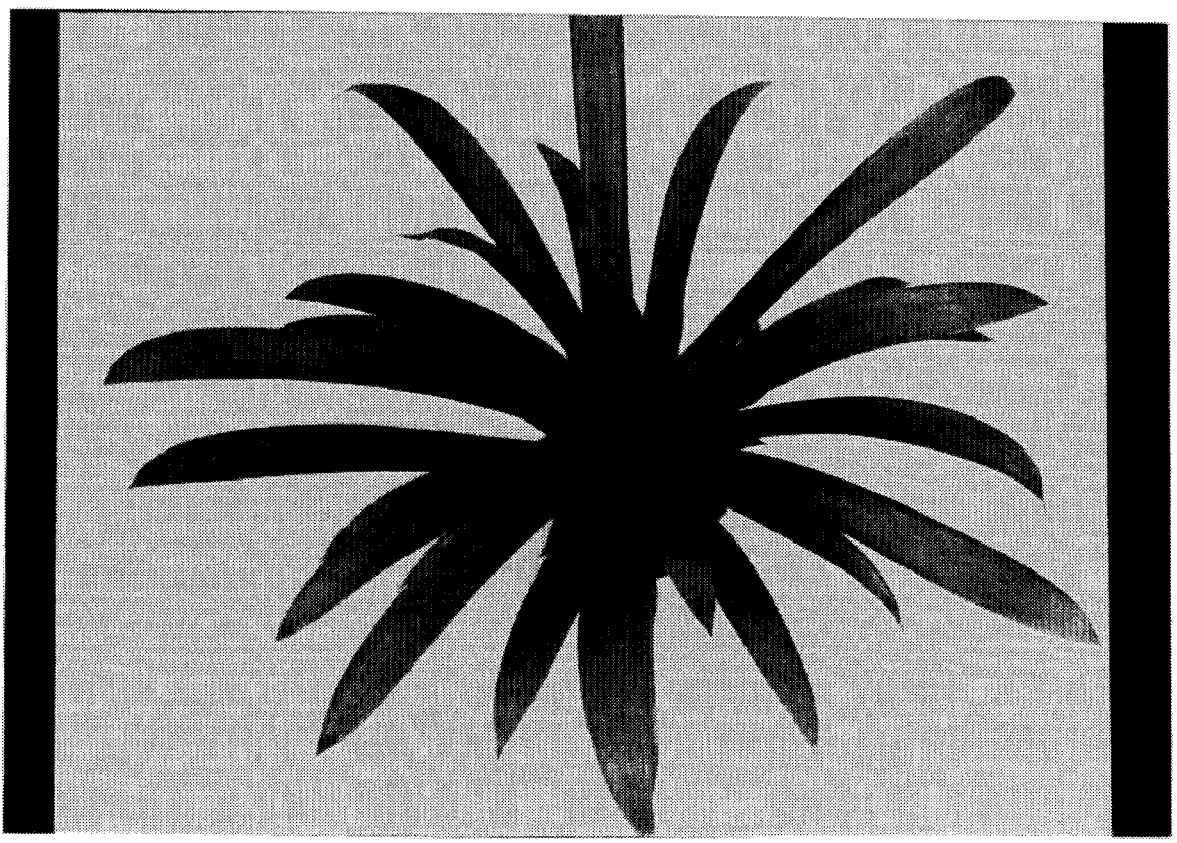
FIG. 1 comprises a top perspective view of a full plant with floral bracts, and wherein the bract color is accurately depicted.
Figure 2:
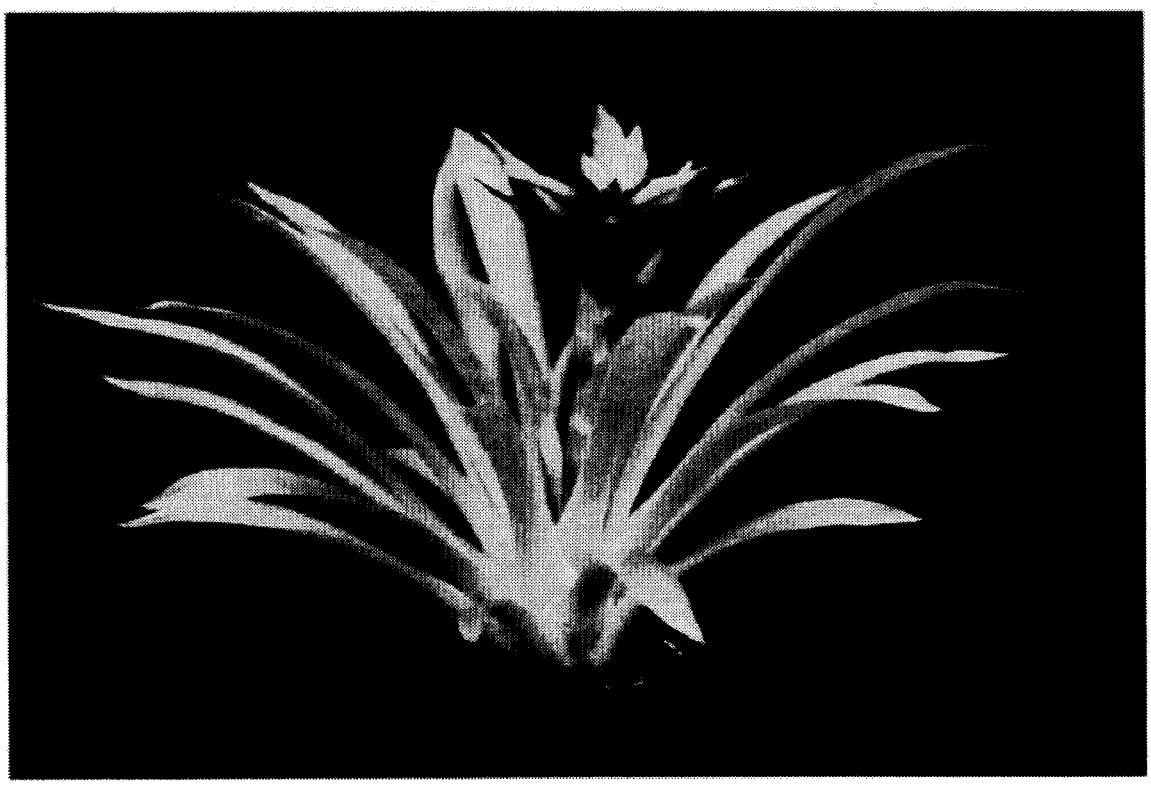
FIG. 2 is a side view showing foliage and inflorescence of a specimen plant.
Figure 3:
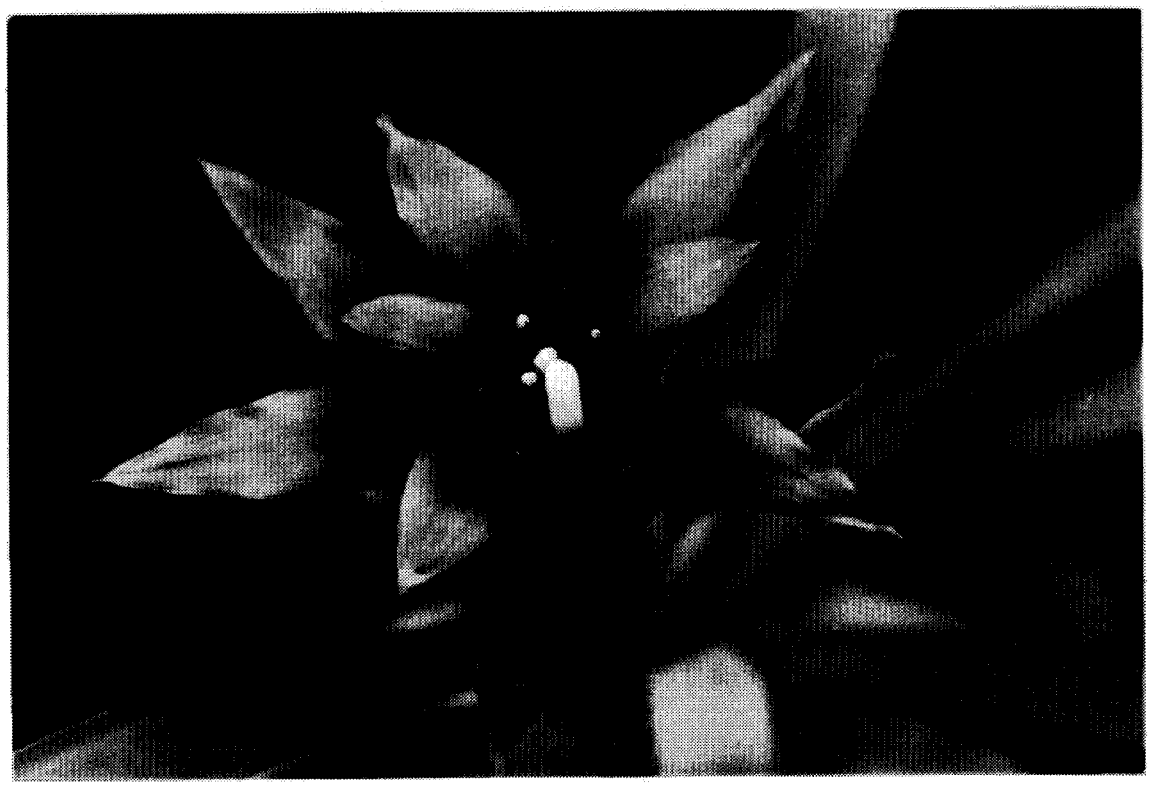
FIG. 3 is a more enlarged showing of the floral bracts and inflorescence. The floral bract color of FIGS. 2 and 3 are not correct, with the true bract color shown in the photograph of FIG. 1.

The new cultivar 'Ultra' is a product of a planned breeding program and was originated by the inventors from a cross made during such a program in Assendelft, The Netherlands, in 1985. The male, or pollen parent, was an unnamed selection from a mutation of *Guzmania ligulata* ligulata, identified by Code Number 84336128. The female, or seed parent, was an unnamed cultivar of *Guzmania ligulata* minor, identified by the Code Number 8433655. Both parents have a degree of homozygosity such that the progeny of the cross were and continue to be surprisingly uniform. The selection comprising the new variety was chosen after commencement of flowering of the progeny in 1987, and subsequent asexual propagation by offshoots has demonstrated that the combination of characteristics as herein disclosed for the new cultivar 'Ultra' are firmly fixed and are retained through successive generations of asexual reproduction.

'Ultra' has been deposited at the American Type Culture Collection, 12301 Parklawn Drive, Rockville, Md., U.S.A., and has been accorded accession No. 758525.

'Ultra' is particularly characterized by the following combination of characteristics:

1. Strong, compact growth habit.
2. Dark purple inflorescence.
3. Superior floral bract production.
4. Star shaped inflorescence.
5. Relatively small in overall size and diameter when compared to other cultivars of this general type.

The closest comparison cultivar is "Empire". Most of the characteristics described below for 'Ultra', except for the color of the inflorescence, are generally similar to those same characteristics of 'Empire'. The floral bract color of the respective cultivars is very dissimilar. Whereas the bract color of 'Empire' is a bright red, the bract color of 'Ultra' is a deep purple, referred to in the color chart as a greyed-purple. Such color is very distinctive.

'Ultra' has not been tested under all available environmental conditions. The phenotype may slightly vary with variations in environmental conditions such as temperature, light intensity, day length and humidity, as well understood by those skilled in the art, without, however, any variance in genotype.

In the following description, color references are made to the Royal Horticultural Society Colour Chart (R.H.S.).

The following traits have been repeatedly observed and in combination distinguish 'Ultra' as a new and distinct cultivar. These observations, measurements and descriptions have been performed under greenhouse conditions in Assendelft, The Netherlands.

Plant
    Form—Funnel form rosette.
    Height—Short; approximately 20 cm high when flowering.
    Growth habit—Stemless.
    Diameter—Approximately 45 cm at time of flowering.
Foliage
    Size of leaf—Approximately 27 to 30 cm long; leaves extend away from the base to form a full plant.
    Shape of leaf—Linear lanceolate.
    Surface texture—Smooth.
    Variegation—None.
    Color—Upperside; 146A; Underside; 146B; with greater amounts of fertilizer, the color can become slightly darker, in the range of 137A (upperside) and 137B (underside). During flowering, the center leaves can be infused in the middle with purple, approximately 186A.

Bracts
- Length—Approximately 8 to 14 cm.
- Scape bracts: Approximately 6 to 10 cm.
- Primary bracts: Approximately 6 to 10 cm.
- Floral bracts: Approximately 5.5 cm.
- Width—Scape and primary bracts are approximately 2.5 cm, floral bracts approximately 1.4 cm.
- General shape—Ovate lanceolate.
- Texture—Smooth.
- Margin—Entire
- Color—
  - Upperside: When bud just opening 187A, becoming 187B during flowering; color of middle part of bracts toward center is 187C.
  - Underside: 187D.

Flowers
- Borne—Erect on stalks, length of inflorescence being approximately 6 cm.
- Shape of inflorescence—Head.
- Individual petals—
- Length: Approximately 5 cm.
- Width: Approximately 0.5 cm.
- Quantity: Approximately 30 flowers, depending on the size of plant.
- Color of petals: R.H.S. 155D at top 0.3 cm; next approximately 1 cm is 8A, with color below that area becoming more translucent.
- Time of blooming: In fully grown plant, flowers can bloom the whole year starting approximately 12 weeks after acetylene treatment.
- Duration of blooms: Each flower blooms 1 day and the total during of blooming is about 6 weeks.

Reproductive organs
- Ovaries—Superior.
- Stamens—6 in number.

Seed characteristics
- Quantity—Approximately 5,000 seeds divided over approximately 20 capsules.
- Texture—The seeds are plumose.
- Other—Not every plant has seed since not every plant makes seed. The seeds cannot be used for reproduction since characteristics cannot be passed through sexual propagation.

What is claimed is:

1. Guzmania plants produced from deposited seeds having ATCC accession No. 75825.

2. Guzmania seeds having ATCC accession No. 75825.

* * * * *

UNITED STATES PATENT AND TRADEMARK OFFICE
CERTIFICATE OF CORRECTION

PATENT NO. : 5,453,563
DATED : September 26, 1995
INVENTOR(S) : BAK et al.

It is certified that error appears in the above-indentified patent and that said Letters Patent is hereby corrected as shown below:

Cover Page, item [45], an --*-- should appear before the grant date of "Sep. 26, 1995";

item [75], "Geradus" should read --Gerardus--;

item [73], "Corn. Bak B.B." should read --Corn. Bak B.V.--;

After item [73], the following should appear: --[*] Notice: The portion of the term of this patent subsequent to May 4, 2010 has been disclaimed--;

item [57], line 1, "'U'" should read --'Ultra'--.

Column 1, line 1, "'ULTRA+2" should read --'ULTRA'--;

line 46, "*ligulata*" should read --*lingulata*--.

UNITED STATES PATENT AND TRADEMARK OFFICE
CERTIFICATE OF CORRECTION

PATENT NO. : 5,453,563
DATED : September 26, 1995
INVENTOR(S) : BAK et al.

It is certified that error appears in the above-indentified patent and that said Letters Patent is hereby corrected as shown below:

Column 2, line 7, "*ligulata*" should read --*lingulata*--;

line 8, "*ligulata*" should read --*lingulata*--;

line 10, "*ligulata minor*" should read --*lingulata minor*--;

line 22, "758525" should read --75825--.

Signed and Sealed this

Thirtieth Day of January, 1996

Attest:

BRUCE LEHMAN

Attesting Officer

Commissioner of Patents and Trademarks